(12) United States Patent
McGrath

(10) Patent No.: US 11,666,696 B2
(45) Date of Patent: Jun. 6, 2023

(54) ENTEROSTOMY DRAINAGE METHODS AND DEVICES

(71) Applicant: Ellen McGrath, Canton, MA (US)

(72) Inventor: Ellen McGrath, Canton, MA (US)

( * ) Notice: Subject to any disclaimer, the term of this patent is extended or adjusted under 35 U.S.C. 154(b) by 173 days.

(21) Appl. No.: 16/813,877

(22) Filed: Mar. 10, 2020

(65) Prior Publication Data

US 2020/0306429 A1 Oct. 1, 2020

Related U.S. Application Data

(60) Provisional application No. 62/823,074, filed on Mar. 25, 2019.

(51) Int. Cl.
*A61M 1/00* (2006.01)
*A61M 25/10* (2013.01)
*A61M 39/20* (2006.01)

(52) U.S. Cl.
CPC .......... *A61M 1/90* (2021.05); *A61M 25/1002* (2013.01); *A61M 25/1025* (2013.01); *A61M 39/20* (2013.01); *A61M 1/964* (2021.05); *A61M 2202/068* (2013.01); *A61M 2210/106* (2013.01)

(58) Field of Classification Search
CPC ...... A61M 1/90; A61M 1/86; A61M 25/1002; A61M 25/1025; A61M 39/20; A61M 1/964; A61M 2202/068; A61M 2210/106; A61M 25/1011; A61M 2210/1064; A61M 25/10; A61M 25/0068; A61F 5/442; A61F 5/445; A61F 2005/4455; A61J 15/0042; A61J 15/0038
See application file for complete search history.

(56) References Cited

U.S. PATENT DOCUMENTS

| | | | |
|---|---|---|---|
| 3,777,757 A * | 12/1973 | Gray | A61M 25/02 604/99.04 |
| 3,915,171 A | 10/1975 | Shermeta | |
| 3,937,224 A | 2/1976 | Uecker | |
| 4,368,739 A | 1/1983 | Nelson, Jr. | |
| 4,666,433 A | 5/1987 | Parks | |
| 4,676,778 A | 6/1987 | Nelson, Jr. | |
| 4,772,260 A | 9/1988 | Heyden | |
| 4,911,163 A | 3/1990 | Fina | |
| 5,234,454 A | 8/1993 | Bangs | |
| 5,242,395 A | 9/1993 | Maglinte | |
| 5,261,898 A * | 11/1993 | Polin | A61F 5/445 604/327 |
| 5,458,583 A | 10/1995 | McNeely et al. | |
| 5,591,128 A | 1/1997 | Sithole | |

(Continued)

FOREIGN PATENT DOCUMENTS

| | | |
|---|---|---|
| CN | 201139784 Y | 10/2008 |
| WO | 2012134196 | 10/2012 |

*Primary Examiner* — Erich G Herbermann
*Assistant Examiner* — Alessandro R Del Priore
(74) *Attorney, Agent, or Firm* — Lambert Shorten & Connaughton; David J. Connaughton, Jr.; Justin P. Tinger

(57) ABSTRACT

The present disclosure provides tubes of the draining of liquid from enterostomies. In accordance with aspects and embodiments, an enterostomy tube is provided for draining liquid stool from the gastrointestinal tract, the enterostomy tube having a flared, internal end with scalloped edges and openings around the circumference to enhance collection and an ovular balloon to better fit within the intestinal tract.

16 Claims, 7 Drawing Sheets

(56) References Cited

U.S. PATENT DOCUMENTS

| | | | | |
|---|---|---|---|---|
| 5,609,597 | A * | 3/1997 | Lehrer | A61B 17/12013 |
| | | | | 606/139 |
| 6,585,720 | B2 | 7/2003 | Lapcevic | |
| 9,211,234 | B2 | 12/2015 | Tai et al. | |
| 9,452,081 | B2 | 9/2016 | Forsell | |
| 9,867,915 | B1 | 1/2018 | Daggett | |
| 2005/0124932 | A1 * | 6/2005 | Foster | A61M 25/10 |
| | | | | 604/99.04 |
| 2006/0052813 | A1 * | 3/2006 | Nobles | A61M 25/1011 |
| | | | | 606/194 |
| 2007/0049878 | A1 | 3/2007 | Kim et al. | |
| 2008/0275402 | A1 * | 11/2008 | Schnell | A61F 5/445 |
| | | | | 604/175 |
| 2011/0282311 | A1 * | 11/2011 | Nishtala | A61F 5/4405 |
| | | | | 604/332 |
| 2012/0136324 | A1 * | 5/2012 | Hanuka | A61F 5/441 |
| | | | | 604/318 |
| 2017/0135846 | A1 * | 5/2017 | Weiss | A61F 5/445 |
| 2019/0358438 | A1 * | 11/2019 | Fortune | A61M 27/00 |
| 2020/0046384 | A1 * | 2/2020 | Ciccone | A61M 3/022 |
| 2020/0179630 | A1 * | 6/2020 | Chun | A61M 16/0488 |
| 2020/0297585 | A1 * | 9/2020 | Iyunni | A61J 15/0092 |

* cited by examiner

ENTEROSTOMY DRAINAGE METHODS AND DEVICES

FIELD OF DISCLOSURE

The present disclosure relates to ostomy supplies and more specifically, to tubes designed to drain gastrointestinal fluid from enterostomies.

BACKGROUND

Ostomy surgery is a life-saving medical procedure used to reroute bodily waste through a surgically created stoma. A stoma is a small opening on the abdomen where which waste can be excreted from the body and collected in an ostomy bag, sometimes referred to simply as a pouch, worn over the stoma. Ostomy surgery may be necessary due to birth defects or as a result of medical conditions, including but not limited to inflammatory bowel disease, diverticulitis, incontinence, and cancer. Ostomy surgery may also be necessary in cases of severe abdominal and pelvic trauma. Ostomies may be temporary or permanent, but regardless of the timeframe in which a patient has an ostomy, it is life-changing.

The three most common types of ostomies are colostomies, urostomies, and ileostomies. In a colostomy, a portion of colon or rectum is removed, and the remaining colon is brought through the abdominal wall. The surgically created opening of the colon, i.e., the large intestine, at the abdominal wall, results in a stoma that allows for the excretion of waste. A urostomy is a general term for surgical procedures which divert urine away from a dysfunctional, diseased, or removed, bladder. A conduit at either the beginning of the small bowel (the ileum) or at the beginning of the large intestine (cecum) is surgically removed and relocated as a conduit for urine to pass from the kidneys through a stoma. In an ileostomy, an opening is created from the lowest part of the small intestine, the ileum. The ileum is brought through the abdominal wall to from a stoma. Other examples of ostomies include, but are not limited to, jejunostomy and duodenostomy and gastrostomy. In a jejunostomy, an opening is created through the skin into the jejunum, a part of the small intestine, that can be used as a feeding tube or as a bypass during bowel resection. In a duodenostomy, the first part of the small intestine, the duodenum, is surgically removed and brought through the abdominal wall to create a stoma. In a gastrostomy, a stoma is created on the abdomen into the stomach.

Ostomies that are formed further down the intestinal tract, like colostomies, tend to excrete solid and more formed stool as a result of their location in the digestive pathway, and stoma bag appliances are generally used with high success rates and little complications. In contrast, however, ostomies that are formed further up the intestinal tract, like ileostomies, duodenostomies, and duodenostomies, and ostomies at the stomach, referred to herein as proximal stomas, drain liquid stool.

Stoma bags are not however designed to drain liquid. Stoma bags are generally attached to the skin of the abdomen around the stoma with glue to collect stool. Liquid stool however is often heavy and causes the stoma bag to disconnect from the abdomen and/or leak out of the bag onto the surrounding skin. The liquid stool excreted from the body from proximal stomas contains high concentrations of gastric acid and intestinal fluid and can cause skin damage, erosion, and pain.

Currently, no standard of care exists for draining of stool from proximal stoma and no tubes exist that are intended for stoma liquid stool drainage. Absent proper draining, however, stoma bags cannot stay attached and patients suffer skin burns, pain, discomfort, and excoriation.

Studies outlining incidence of skin erosion around stomas suggest that up to 75% of people with an ostomy experience a peristomal skin complication. Source: Rapp C G, L Richbourg, J M Thorne. Difficulties Experienced by the Ostomate After Hospital Discharge. JWOCN. 2007; 34(1): 70-79. Therefore, there is a need in the art for a device which can solve the problems of stoma bag leakage and proper stool drainage.

SUMMARY OF DISCLOSURE

The present disclosure is directed to improved devices and methods for draining liquid from proximal ostomies, i.e., enterostomies, including the draining of liquid stool from the gastrointestinal tract. In accordance with aspects and embodiments, an ostomy device is provided comprising an elongate tube having a tube body of substantially uniform diameter, the elongate tube comprising a first end and a second end, wherein the first end has a diameter greater than the diameter of the tube body. The device further includes a balloon surrounding the tube body proximate to the first end of the tube, a balloon port in fluid communication with the balloon, the balloon port located within the tube body; and a balloon port opening in fluid communication with the balloon port, the balloon port proximate the second end of the tube.

In accordance with embodiments, the balloon is deflated in a first, uninstalled state, and inflated in a second, installed state. In some embodiments, the first end may have a scalloped edge and may include a plurality of openings adjacent the edge, and the balloon may have an ovular shape. The first end may further be comprised of flexible material that may be cinched such that the diameter is reduced to a diameter equal to or less than the diameter of the tube body. The balloon may be inflated via the balloon port/balloon port opening by injecting sterile solution into the balloon port. The second end of the tube may be fit with a collection device or may comprise a cap that covers the second, open end. In some embodiments, the tube body may further include a vent.

In accordance with aspects and embodiments, a method of draining liquid from an enterostomy is provided, the method comprising using the disclosed enterostomy device in a patient with an enterostomy. The method comprises inserting the disclosed enterostomy device, with the first end cinched and the balloon deflated, into the stoma, traversing the subcutaneous abdomen fat, and inserting the device into the gastrointestinal tract such that balloon is positioned within the intestine walls and/or abuts the stomach wall. The first end is then uncinched and allowed to expand and the balloon is inflated. Gastrointestinal fluid is collected by the tube. The second end may either be capped to prevent leakage of fluid, for example when collection bags are being changed, or may be connected to a collection bag to collect drained fluid.

DETAILED DESCRIPTION

Figure 1:
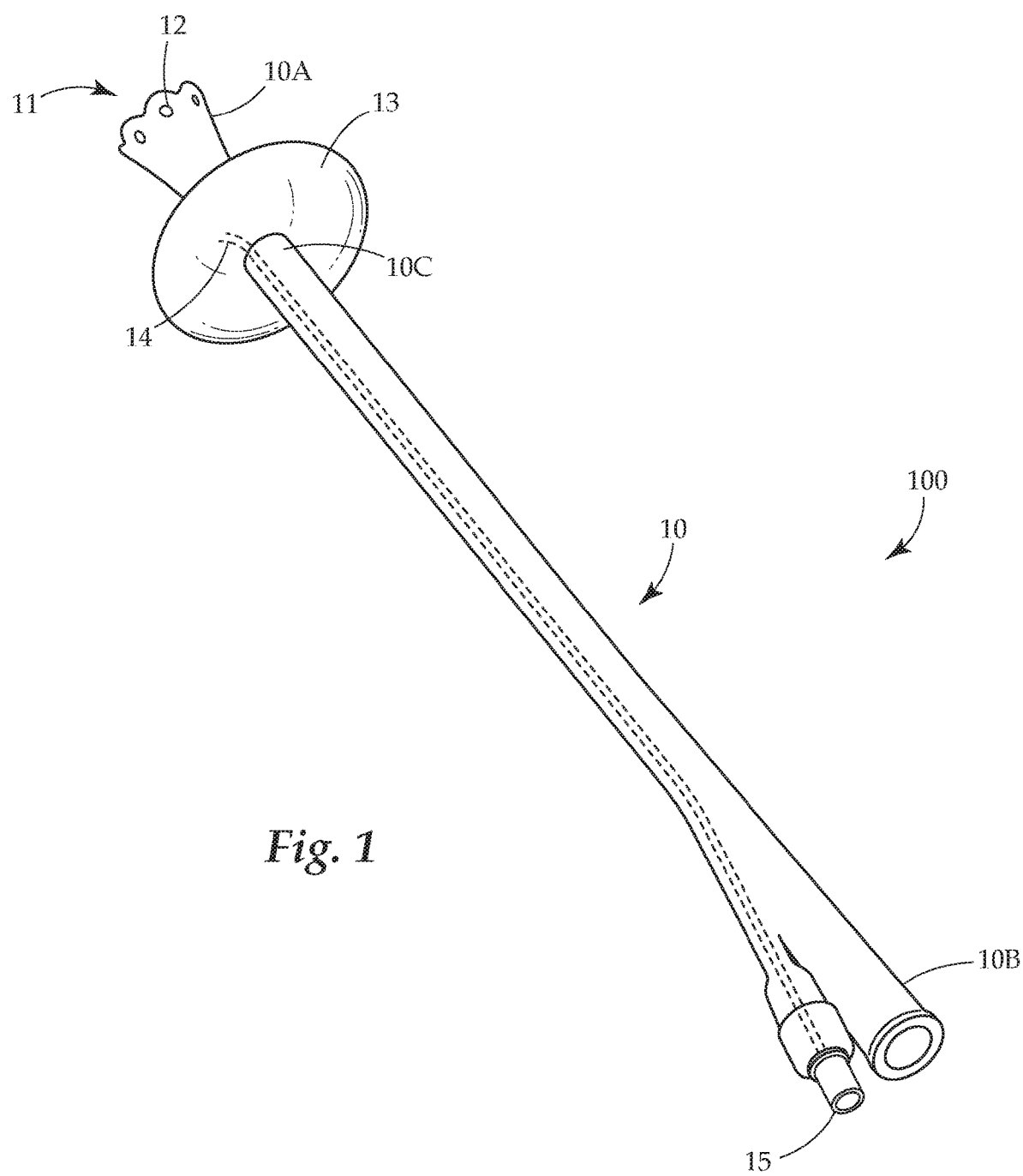
FIG. 1 is an enterostomy tube in accordance with aspects and embodiments of the disclosure.

The present disclosure provides an enterostomy tube for draining liquid, gastric liquid and/or liquid stool, from the stomach and ostomies located in the small intestine, referred to herein as proximal ostomies and enterostomies, interchangeably. Proximal ostomies include, but are not limited, to duodenostomies, ileostomies, and jejunostomies. The disclosed ostomy tool advantageously provides for draining of liquid stool from an ostomy, which prevents leakage of stool onto skin. Liquid stool contains caustic biological material which burns the skin surrounding the stoma, causing damage. The tubes of the present disclosure allow for drainage and thus allow for the skin surrounding proximal ostomy stomas to heal. The disclosed tubes may also be used to drain liquid from the stomach via a gastrostomy and may be used, for example, when a patient has a bowel obstruction to empty gastric fluid and prevent vomiting.

The current standard of ostomy care does not have tubes designed specifically for gastric and small intestine drainage. Liquid from gastrostomies is currently drained via a feeding tube with a small opening about 1-2 mm wide. Proximal ostomy drainage is collected in stoma bags attached directly to the abdominal skin surround the stoma. In many cases, the excreted liquid stool is heavy and leaks out of the bag onto the skin, burning the skin and causing the ostomy bag to fall off. In some cases, tubing designed for other medical uses is often inserted into proximal ostomy stomas in an attempt to drain liquid stool when the skin cannot hold a ostomy bag. These tubes are designed for other parts of the body and/or other uses and thus perform poorly for draining liquid stool.

For example, MIC and MIC*KEY feeding tubes and foley catheters have been used in an attempt to adequately drain liquid stool from enterostomies and stomach contents from gastrostomies. Although these tubes generally have balloons to hold them in place, they have single small openings, making them poor performers at draining gastric contents and liquid stool. Additionally, the balloons designed to hold these tubes in place are designed for abutting the interior stomach/bladder wall. When used in the intestine, the size and shape of these balloons can interfere the flow of contents above the tube/balloon, creating risk of blockage.

Other makeshift drainage "solutions" include surgical drains and catheters designed for other various medical procedures, none of which include the draining of liquid stool from proximal ostomy. These devices are often made of materials that are too hard and/or do not have a mechanism to hold the drainage tube in place, requiring the tube to be sutured into position.

The present disclosure provides a tube that can drain gastric contents and intestinal fluids from the stomach and intestine from any point along the gastrointestinal tract that produces liquid stool, up to the colon. The disclosed tube advantageously includes a balloon shaped to lie flat against the inside of the intestinal wall and an opening within the intestine designed accommodate mucus and sediments mixed with stool such that it can be removed from the intestine via the tube. The opening of the tube to be inserted into the stomach/intestine via the stoma is advantageously flexible and able to be cinched into a closed position for insertion and released after being positioned in the body. The disclosed tube may also include a vent to further facilitate the passage of gas from the gastrointestinal tract. The disclosed drainage tube may reduce the noise associated with waste excretion via enterostomy (ie flatus). The disclosed tube may thus not only enhance patient comfort by allowing the skin surrounding stoma to heal and preventing further damage but may also improve patient confidence and quality of life.

In accordance with aspects and embodiments, an enterostomy tube 100 is provided in accordance with FIG. 1. FIG. 1 shows ostomy tube 100 in an installed state. Tube 100 has tube body 10 having internal end 10A and external end 10B. Internal end 10A terminals in scalloped edge 11. Scalloped edge 11 ensures that when in the body, end 10A and edge 11 do not stick to gastrointestinal surfaces. End 10A further includes a plurality of openings 11 around the circumference of end 10A proximate edge 11. The circumference and therefore diameter of end 10A greater than the diameter of tube body 10. Tube body 10 has thereon balloon 13 at position 10C. Balloon 13 has a height that is less than its width, creating a balloon shape that is oval, i.e., flatter than a sphere. The height of balloon 13 corresponds to a length of tube body 10. The diameter of tube body 10 increases in diameter at a position on tube body 10 equal to position 10C plus the height of balloon 13. The diameter of tube body 10 increases to terminate in edge 11, creating a conical end 10A.

Tube body 10 further includes therein balloon port 14 having port in communication with balloon 13 and balloon port opening 15. Balloon port opening 15 branches off tube body 10 such that opening 15 is proximate external end 10B.

In preferred embodiments, tube body 10 has a 1 cm or a 2 cm diameter. At these preferred embodiments, standard ostomy appliances may be connected to external end 10B, however other diameters of tube body 10 may also be used. Opening 15 is sized to receive a Fit Leur Lock syringe. Appropriate sizes of tube 10 and opening 15 and other parts of the disclosed ostomy tube, as well as materials for fabrication and use, will be readily apparent to those of skill in the art.

Figure 2:
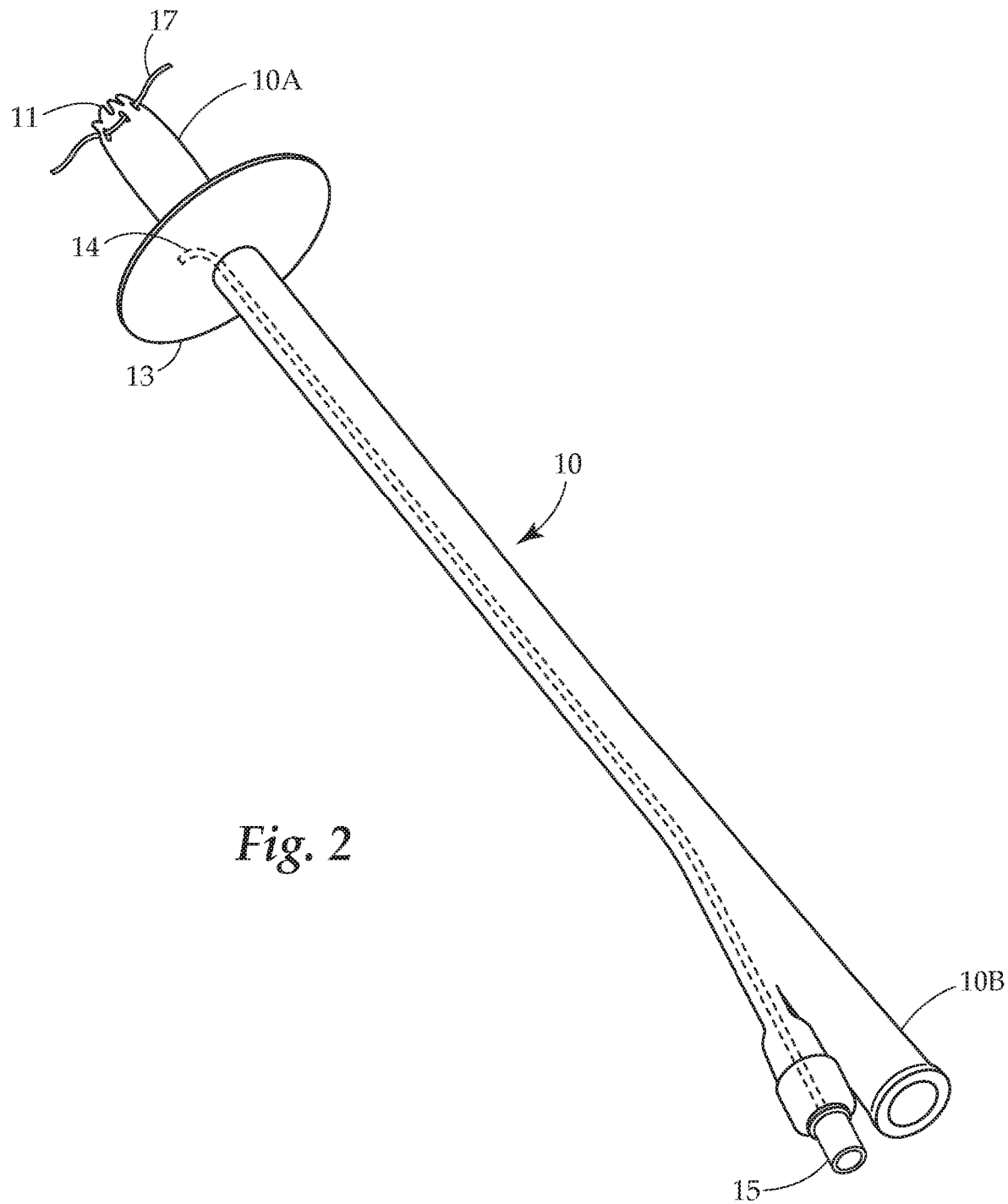
FIG. 2 is an enterostomy tube in accordance with aspects and embodiments of the disclosure.

FIG. 2 shows ostomy tube 100 in a pre-installed/inserted state. As can be seen in the figure and in contrast to FIG. 1, end 10A of tube body 10 is cinched into a diameter equal to or less than the diameter of tube body 10. End 10A is cinched with suture 17 or a similar medical appliance that can be easily and readily removed once enterostomy tube 1000 is in a patient. Alternatively, end 10A may simply hold a substantially cinched shape while being inserted into the narrow space of a stoma and flare outward upon entry into the more unrestricted space of the stomach/intestine. Still referring to FIG. 2, balloon 13 is not inflated and rather than having a substantially firm volume, as in FIG. 1, it is instead a flimsy and unfilled shell. The reduction in diameter of end 10A and reduction in volume and rigidity of balloon 13 make inserting enterostomy tube 100 into an ostomy patient easier.

Figure 3:
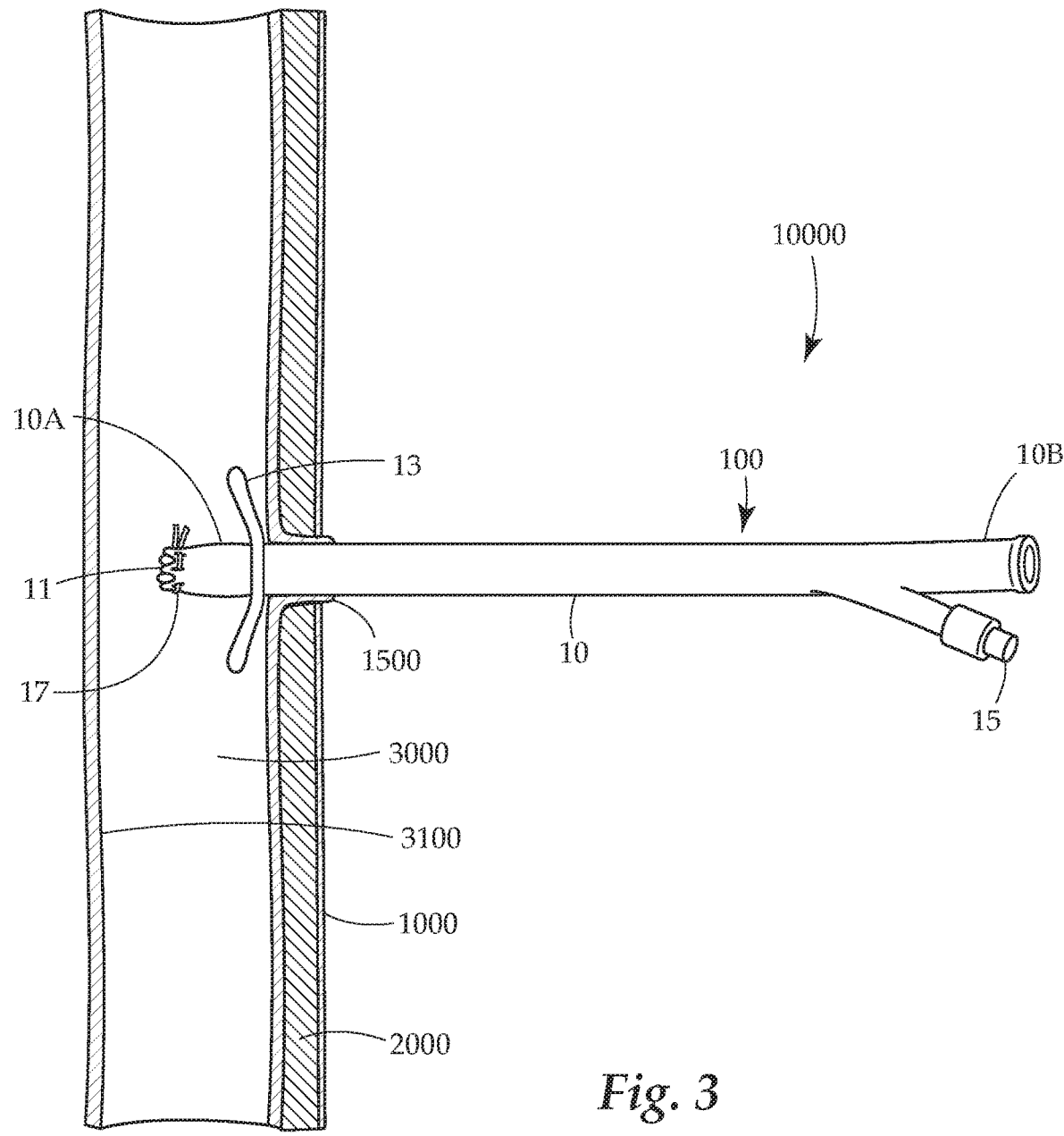
FIG. 3 shows an enterostomy tube inserted into a patient, in accordance with aspects and embodiments of the disclosure.

For example and turning to FIG. 3, system 10000 shows enterostomy tube 100 inserted into a patient having stoma 1500. Enterostomy tube 100 is inserted into stoma 1500 via internal end 10A. End 10A is cinched via suture 17. Cinched end 10A and uninflated balloon 13 are passed through the wall of abdominal skin 1000 and through subcutaneous fat 2000 into intestine 3000 via stoma 1500.

Figure 4:
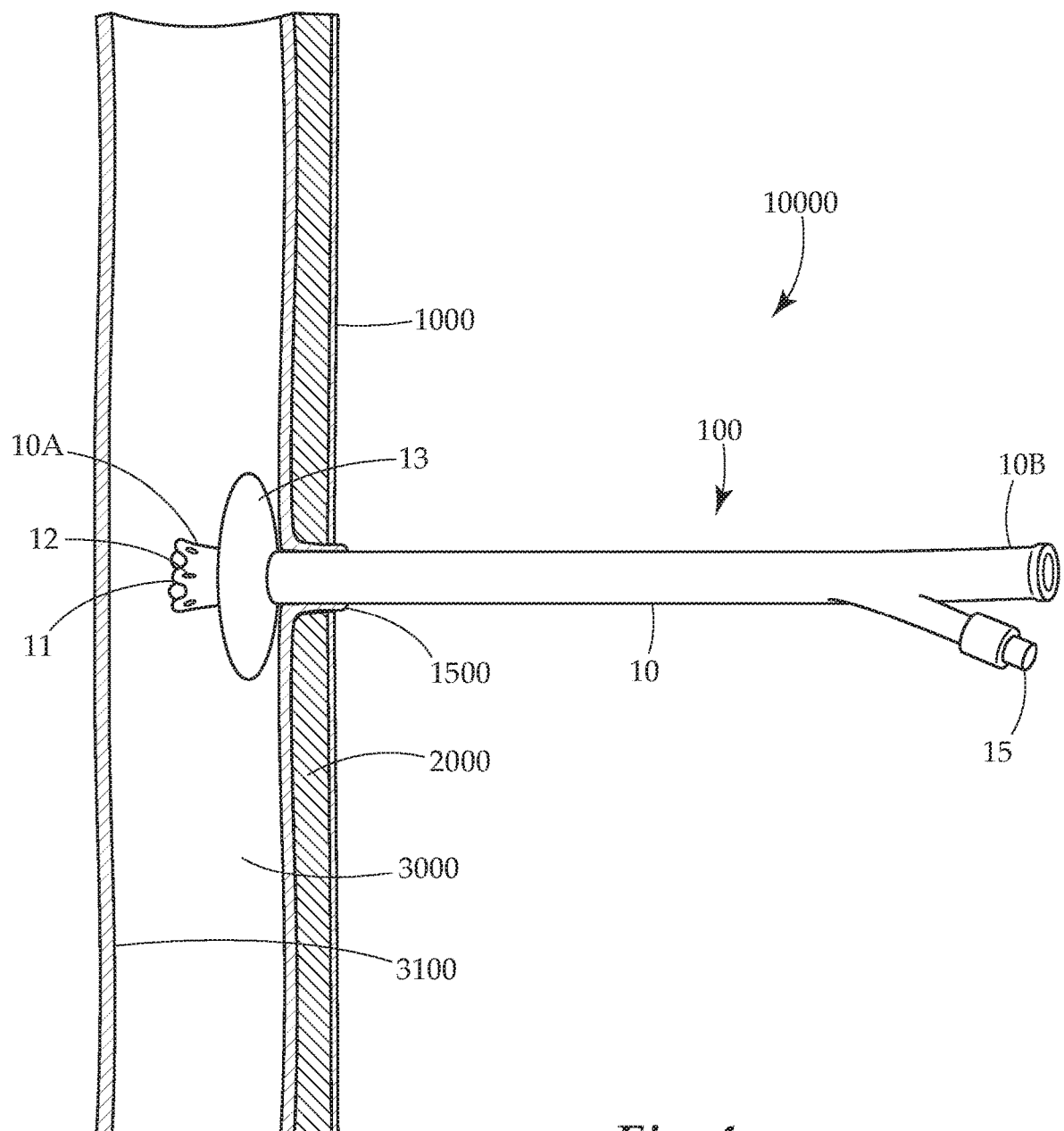
FIG. 4 shows an enterostomy tube inserted into a patient, in accordance with aspects and embodiments of the disclosure.

Turning to FIG. 4, suture 17 is removed and end 10A is allowed to flare open. A Fit Leur Lock syringe is connected to balloon port opening 15 and 3-5 ml of sterile water inserted into the port and fill balloon via balloon port 14 (not shown). Inflated balloon 13 abuts internal intestinal wall 3100, holding enterostomy tube 100 in place. The flat, ovular, shape of balloon 14 also allows fits smaller stomach and intestinal areas and ensures that blockages do not occur.

A drainage bag is connected to end 10B (not shown) and a gastrointestinal liquid is collected via end 10A and drained through body 10A, out end 10B, and into a collection bag. The enlarged diameter of end 10A advantageously allows for more gastrointestinal material to be collected by drainage tube 100. Additionally, openings 12 at edge 11 of end 10A also facilitate the collection of liquid as it passes the internal entry port of the drainage tube.

Figure 5:
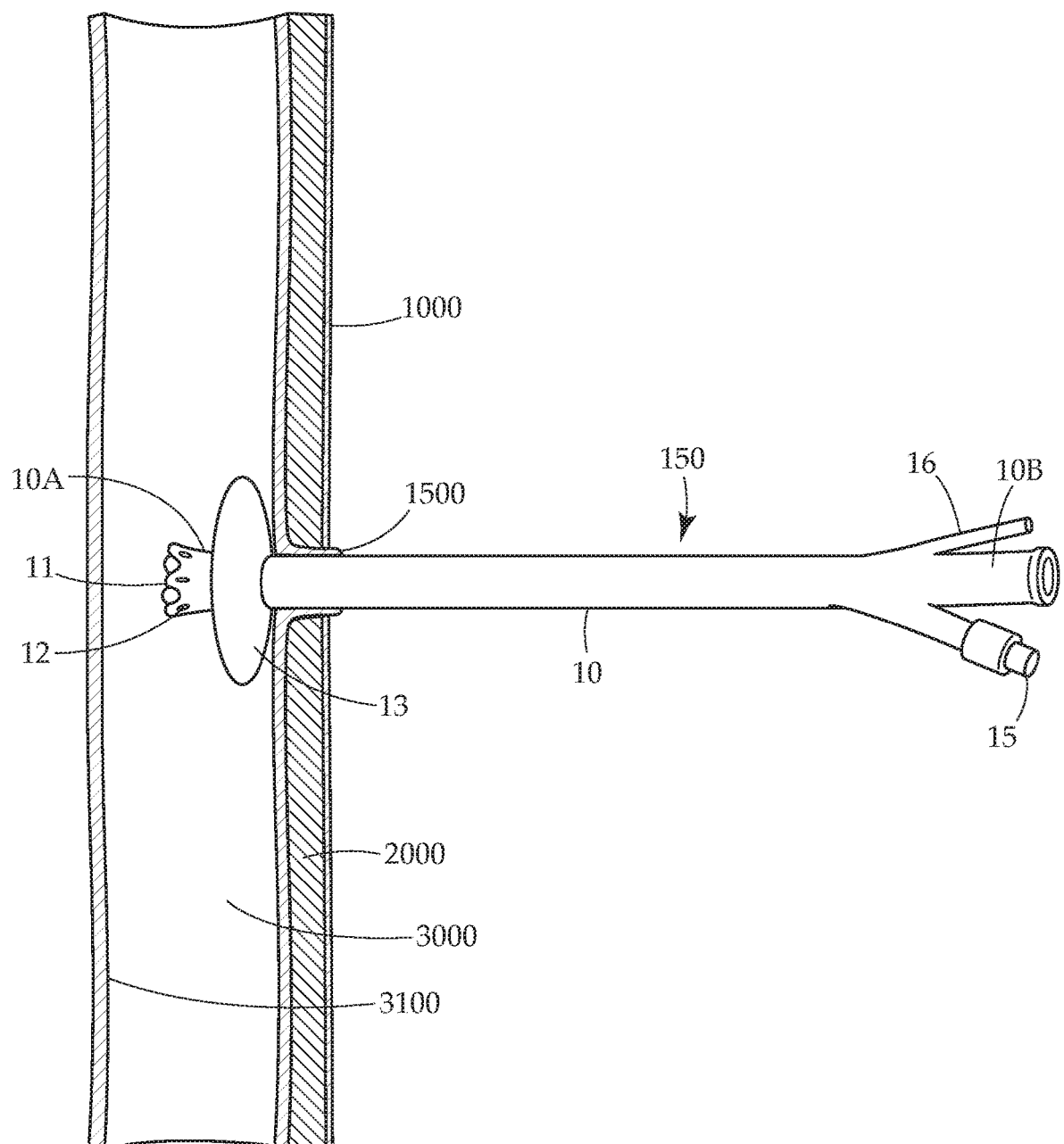
FIG. 5 shows an enterostomy tube inserted into a patient, in accordance with aspects and embodiments of the disclosure.

In accordance with embodiments and referring to FIG. 5, an additional vent may be included in the disclosed enterostomy tube. For example and referring to FIG. 5, enterostomy tube 150 may include vent 16. Vent 16 may branch off tube body 10 much like balloon port opening 15. Vent 16 may facilitate the venting of gas from the gastrointestinal tract while simultaneously avoiding an excess of gas buildup in the collection bag connected to end 10B.

Figure 6:
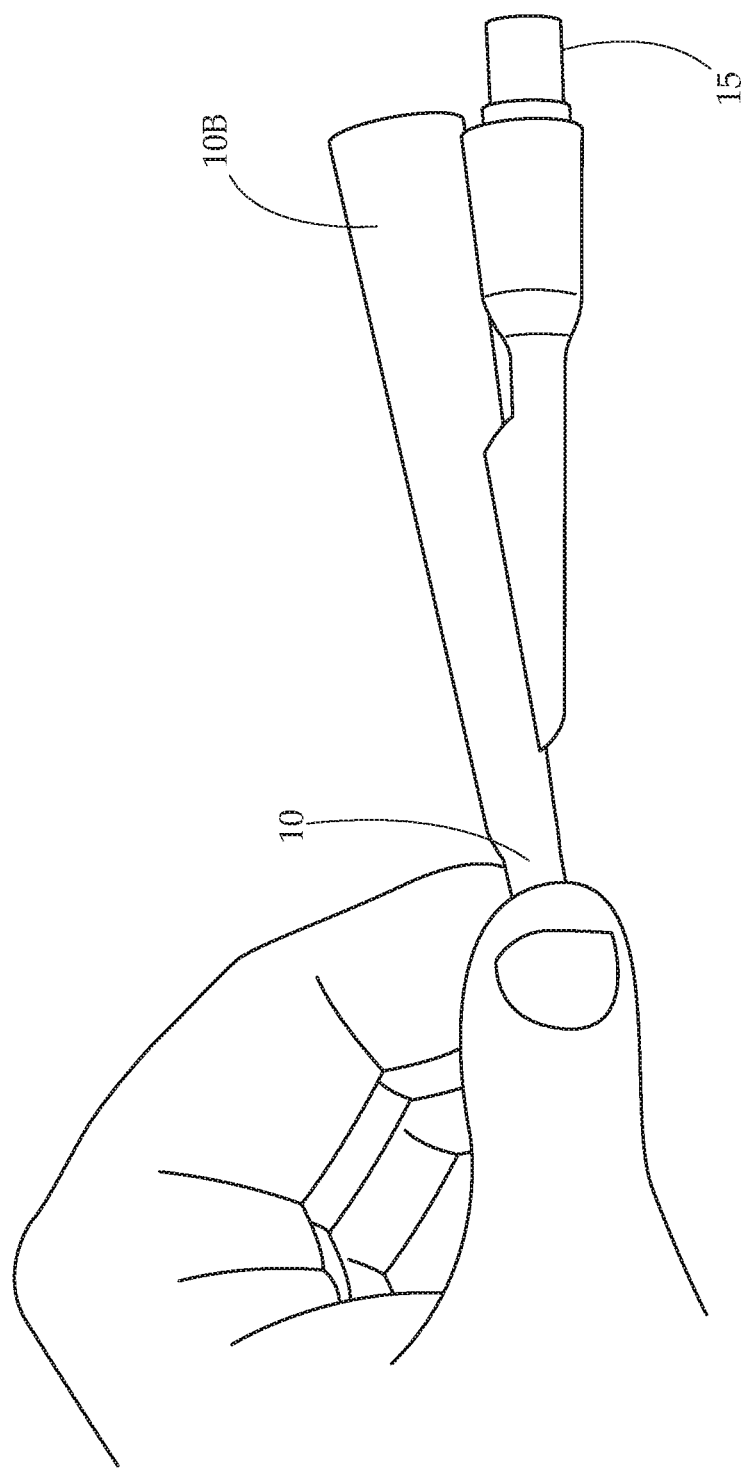
FIG. 6 shows an enterostomy tube inserted into a patient, in accordance with aspects and embodiments of the disclosure.
Figure 7:
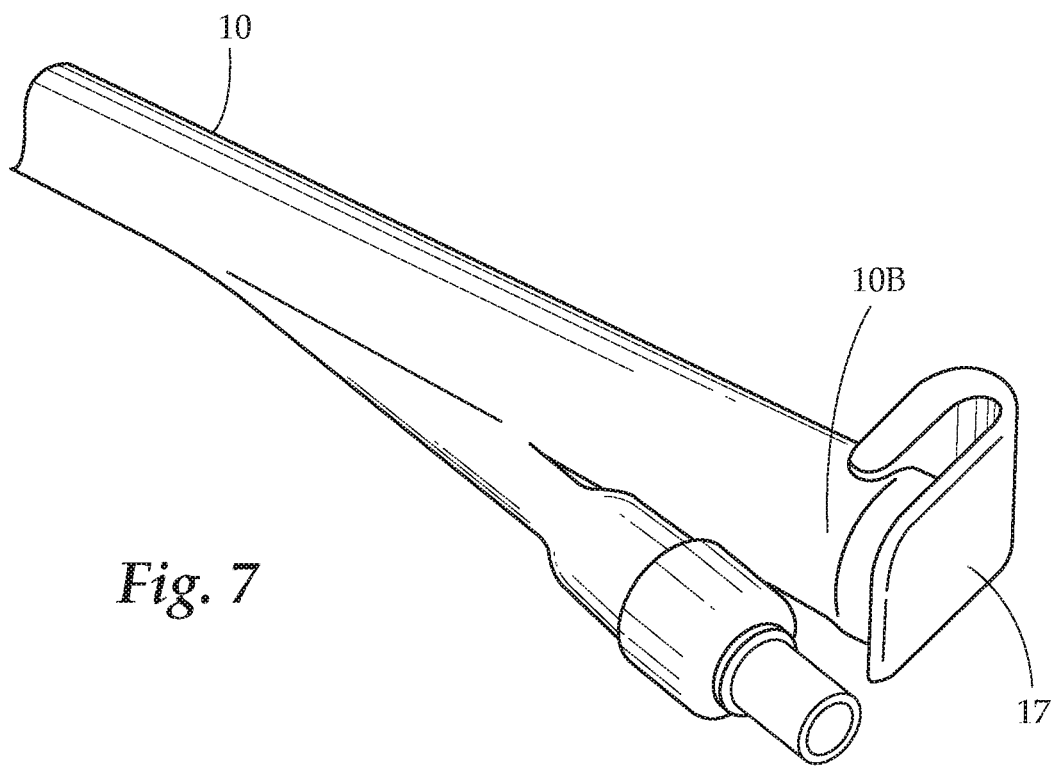
FIG. 7 is a portion of an enterostomy tube and cap in a closed position in accordance with aspects and embodiments of the disclosure.
Figure 8:
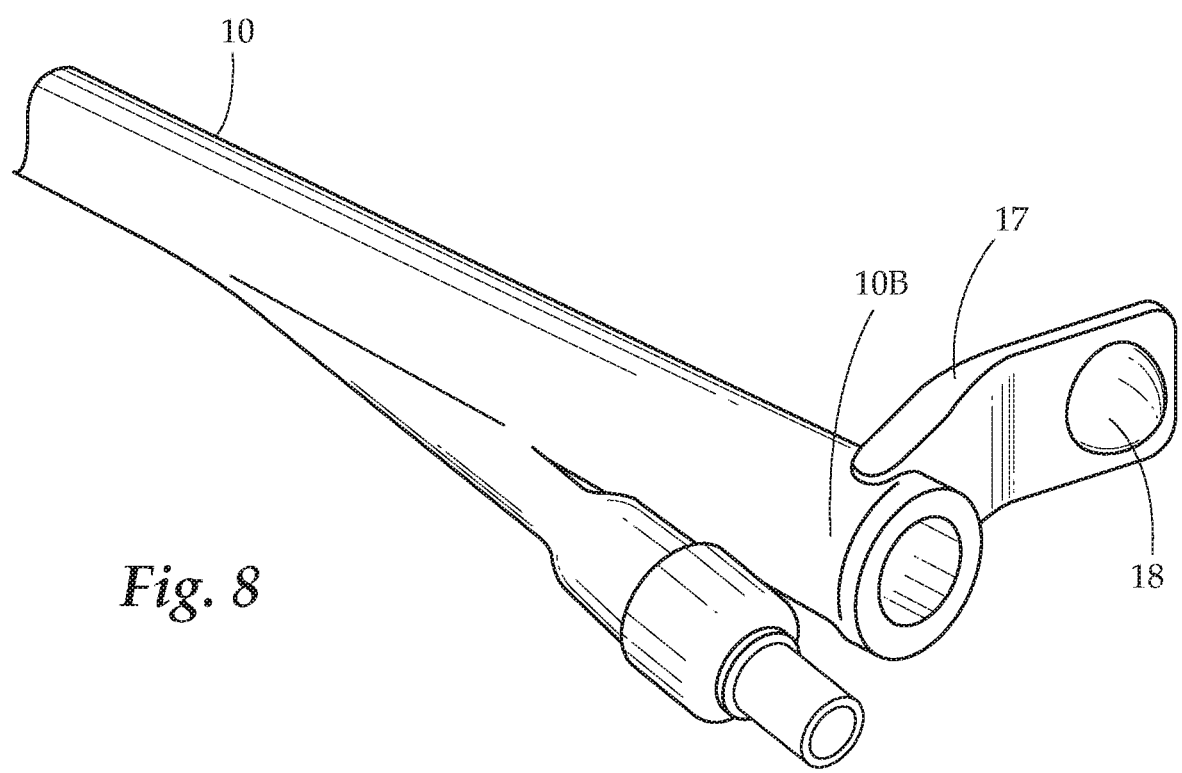
FIG. 8 is a portion of an enterostomy tube and cap in an open position in accordance with aspects and embodiments of the disclosure.

When stoma bags are changed, the disclosed enterostomy tube can be closed to avoid the leaking of intestinal fluid. FIG. 6 shows end 10B uncapped, as it would be when connected to a stoma appliance. FIG. 7 shows end 10B with cap 17. Cap 17 may be used when a stoma appliance is not connected to end 10B. Referring also to FIG. 8, cap 17 may be continuous two sided piece of material, most preferably, a plastic, that may flexibly plug onto end 10B of tube body 10. Cap 17 may for example, and as shown in FIGS. 7 and 8, be flexible so that when in an open position, it extends outwardly away from end 10B (FIG. 8) and flexes closed (FIG. 7) in a closed position with plug 18 which fits into the opening at end 10B. Generally, cap 17 is molded into or otherwise permanently connected to the end 10B.

Referring also to FIG. 7, cap 17 snap fits onto end 10B of drainage tube 100 via plug 18, thus preventing intestinal fluid from exiting tube 100. The single piece, snap-fit nature of cap 17 makes it an easy, inexpensive, and eloquent solution to ensuring leakage does not occur during the changing of ostomy appliances.

The tubes of the present disclosure may further reduce waste products. The current management of ostomies involves single use plastic bags for the collection of stool. Traditional ostomy bags are often changed a few times per week and discarded, resulting in significant annual cost. The disclosed tubes may advantageously be inserted into the stoma and be used for prolonged periods of time. The disclosed tubes may be rinsed and re-inserted many times for as long as the tube is intact and working. The disclosed enterostomy tubes may also be used in connection with a re-usable collection bag that may also be sanitized and re-used, thereby eliminating the need for single use devices.

The disclosed reusable tubes and reusable collection supplies used therewith may thus not only reduce waste but may also result in meaningful cost savings. Given that many patients' ostomies are permanent, these cost savings may be significant factors in the selection of medical supplies and long term care planning.

Although certain representative embodiments and advantages have been described in detail, it will be apparent to those skilled in the art that various modifications and variations can be made in the present disclosure without departing from the scope or spirit of the disclosure. Other embodiments of the disclosure will be apparent to those skilled in the art from consideration of the specification and practice of the apparatuses and methods disclosed herein. It is intended that the specification and examples be considered as exemplary only.

What is claimed is:

1. An ostomy device comprising:
   an elongate tube having a tube body of a uniform diameter, the elongate tube comprising a first end and a second end, wherein the first end has a diameter greater than the diameter of the tube body;
   a balloon surrounding the tube body proximate the first end;
   a balloon port within the tube body and in fluid communication with the balloon;
   a balloon port opening proximate the second end and in fluid communication with the balloon port;
   wherein the elongate tube further comprises a vent tube, and the vent tube branches off the tube body of the elongate tube;
   wherein the balloon is deflated in a first, uninstalled state, and inflated in a second installed state;
   wherein the first end comprises a scalloped edge, the scalloped edge configured to be cinched in the first uninstalled state and flared open in the second, installed state; and
   wherein a first circumference of a first tube position adjacent the flared open scalloped edge proximate the first end is greater than a second circumference of a second tube portion proximate the balloon such that the first and second tube portions are angled obliquely to an opening defined by the scalloped edge when the scalloped edge is in the installed state.

2. The ostomy device of claim 1, wherein the balloon has an ovular shape.

3. The ostomy device of claim 1, wherein the first end has a plurality of openings adjacent the scalloped edge.

4. The ostomy device of claim 3, wherein the first end is comprised of flexible material that can be cinched to a diameter equal to or less than the diameter of the tube body.

5. The ostomy device of claim 4, wherein the tube body has a diameter selected from the group consisting of 1 cm and 2 cm.

6. The ostomy device of claim 5, wherein the balloon is inflated with sterile solution injected into the balloon via the balloon port opening.

7. The ostomy device of claim 6, wherein the balloon is inflated with about 3-5 ml of sterile water.

8. The ostomy device of claim 7, wherein the balloon port opening is sized to connect with a standard Fit Leur Lock syringe.

9. The ostomy device of claim 1, further comprising a cap attached to the elongate tube body, the cap operable to cover the second end of the elongate tube when in a closed position by a plug of the cap fitting into the second end of the elongate tube.

10. A method of draining liquid stool from an enterostomy, the method comprising:
inserting an enterostomy device into a stoma;
the device comprising:
an elongate tube having a tube body of substantially uniform diameter, a first end and a second end, and wherein the first end has a diameter greater than the diameter of the tube body and is cinched by a suture to have a cinched diameter equal to or less than the diameter of the tube body;
the first end comprising a scalloped edge and a plurality of openings adjacent the scalloped edge, the suture threaded through the plurality of openings;
an ovular uninflated balloon surrounding the tube body proximate the first end and connected to the scalloped edge;
a balloon port in fluid communication with the balloon positioned within the tube body;
a balloon port opening in fluid communication within the balloon port proximate the second end;
wherein the elongate tube further comprises a vent tube, and the vent tube branches off the tube body of the elongate tube; and
wherein inserting the enterostomy device includes the steps of inserting the first end of the device into the stoma, through subcutaneous fat, and into a gastrointestinal tract to position the balloon within the walls of the gastrointestinal tract;
removing the suture and allowing the first end to flare open and create an internal entry port such that a first circumference of a first tube portion adjacent the scalloped edge proximate the first end is greater than a second circumference of a second tube portion proximate the balloon such that the first and second tube portions are angled obliquely to the internal entry port defined by the scalloped edge when the suture is removed;
wherein the scalloped edge and the plurality of openings prevent the first end from sticking to the walls of the gastrointestinal tract;
wherein the plurality of openings further facilitates a collection of a liquid as the liquid passes through the internal entry port; and
venting gas through the vent tube to prevent an excess of gas buildup at the second end of the tube body.

11. The method of claim 10, further comprising removing the suture and allowing the first end to expand to a diameter greater than the diameter of the tube body.

12. The method of claim 11, further comprising inflating the balloon by connecting a Fit Leur Lock syringe to the balloon port opening and injecting 3-5 mL of sterile water into the balloon port.

13. The method of claim 12, further comprising allowing gastrointestinal fluid to pass into the tube from the first end of the device.

14. The method of claim 13, further comprising allowing gastrointestinal fluid to exit the tube from the second end of the device.

15. The method of claim 13, further comprising closing the second end of the tube to prevent leaking of gastrointestinal fluid out of the device.

16. The method of claim 10 wherein the plurality of openings are not sutured to the walls of the gastrointestinal tract.

* * * * *